US011039794B2

United States Patent
Mori et al.

(10) Patent No.: US 11,039,794 B2
(45) Date of Patent: *Jun. 22, 2021

(54) MEAL DETECTION METHOD, MEAL DETECTION SYSTEM, AND STORAGE MEDIUM

(71) Applicant: FUJITSU LIMITED, Kawasaki (JP)

(72) Inventors: Tatsuya Mori, Sagamihara (JP); Kazuho Maeda, Kawasaki (JP); Akihiro Inomata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 254 days.

This patent is subject to a terminal disclaimer.

(21) Appl. No.: 16/008,259

(22) Filed: Jun. 14, 2018

(65) Prior Publication Data

US 2018/0368782 A1 Dec. 27, 2018

(30) Foreign Application Priority Data

Jun. 23, 2017 (JP) .............................. JP2017-123739

(51) Int. Cl.
*A61B 5/00* (2006.01)
*A61B 5/024* (2006.01)
(Continued)

(52) U.S. Cl.
CPC ............ *A61B 5/7275* (2013.01); *A61B 5/024* (2013.01); *A61B 5/02438* (2013.01);
(Continued)

(58) Field of Classification Search
CPC ..... A61B 5/7275; A61B 5/024; A61B 5/6284; A61B 5/1123; A61B 5/02438; A61B 5/721; G06K 9/00355; G09B 19/0092
See application file for complete search history.

(56) References Cited

U.S. PATENT DOCUMENTS

2014/0275748 A1 9/2014 Dunki-Jacobs et al.
2014/0377724 A1 12/2014 Hoover et al.
(Continued)

FOREIGN PATENT DOCUMENTS

EP 3231362 A1 10/2017
EP 3372153 A1 9/2018
(Continued)

OTHER PUBLICATIONS

Extended European Search Report dated Oct. 22, 2018 for corresponding European Patent Application No. 18178225.1, 9 pages.
(Continued)

*Primary Examiner* — Mallika D Fairchild
(74) *Attorney, Agent, or Firm* — Fujitsu Patent Center

(57) ABSTRACT

A meal detection method executed by a processor of a computer, the meal detection method includes acquiring first sensing data from a first sensor configured to detect a motion of an arm of a target person; acquiring second sensing data from a second sensor configured to detect a heart rate of the target person; calculating a first evaluation value indicating likelihood that a meal is being performed based on a first feature amount extracted from the first sensing data; calculating a second evaluation value indicating likelihood that the meal is performed based on a second feature amount extracted from the second sensing data; and determining whether the target person has eaten the meal or not, based on the first evaluation value and the second evaluation value.

19 Claims, 15 Drawing Sheets

(51) Int. Cl.
  *A61B 5/11* (2006.01)
  *G06K 9/00* (2006.01)
  *G09B 19/00* (2006.01)

(52) U.S. Cl.
  CPC .......... *A61B 5/1123* (2013.01); *A61B 5/6824* (2013.01); *A61B 5/721* (2013.01); *G06K 9/00355* (2013.01); *G09B 19/0092* (2013.01)

(56) References Cited

U.S. PATENT DOCUMENTS

| | | |
|---|---|---|
| 2015/0313539 A1 | 11/2015 | Connor |
| 2016/0058328 A1 | 3/2016 | Hotta et al. |
| 2017/0249445 A1* | 8/2017 | Devries ................ A61B 5/1455 |
| 2017/0273634 A1* | 9/2017 | Hotta ...................... G09B 5/02 |
| 2017/0360380 A1 | 12/2017 | Mori et al. |

FOREIGN PATENT DOCUMENTS

| | | |
|---|---|---|
| JP | 2007-48180 A | 2/2007 |
| JP | 2011-107768 A | 6/2011 |
| JP | 2011-115508 | 6/2011 |
| WO | 2016/038585 A1 | 3/2016 |
| WO | 2016/092707 | 6/2016 |
| WO | 2016/092707 A1 | 6/2016 |
| WO | 2016/143074 | 9/2016 |
| WO | 2017/077615 A1 | 5/2017 |

OTHER PUBLICATIONS

Rahman, Tauhidur et al.,"Predicting "About-to-Eat" Moments for Just-in-Time Eating Intervention", Digital Health Conference, ACM, Apr. 11, 2016, pp. 141-150, XP058081474.
Amft, Oliver et al.,"Detection of eating and drinking arm gestures using inertial body-worn sensors", Proceedings of the 2005 Ninth IEEE International Symposium on Wearable Computers (ISWC'05), Oct. 18, 2005, pp. 160-163, XP010859544.
U.S. Office Action dated Aug. 14, 2020 for copending U.S. Appl. No. 16/003,871, 12 pages.
Extended European Search Report dated Nov. 16, 2018, for corresponding European Patent Application No. 8176939.9, 8 pages.
U.S. Office Action dated Feb. 21, 2020 for copending U.S. Appl. No. 16/003,871, 19 pages.
U.S. Notice of Allowance dated Jun. 2, 2020 for copending U.S. Appl. No. 16/003,871, 8 pages.
Japanese Office Action dated Feb. 2, 2021 for corresponding Japanese Patent Application No. 2017-123759, with English Translation, 6 pages.
Japanese Office Action dated Feb. 2, 2021 for corresponding Japanese Patent Application No. 2017-123739, with English Translation, 14 pages.
U.S. Corrected Notice of Allowance for copending U.S. Appl. No. 16/003,871, 6 pages.
U.S. Office Action dated Dec. 22, 2020 for copending U.S. Appl. No. 16/003,871, 6 pages.
U.S. Office Action dated Dec. 4, 2020 for copending U.S. Appl. No. 16/003,871, 7 pages.

* cited by examiner

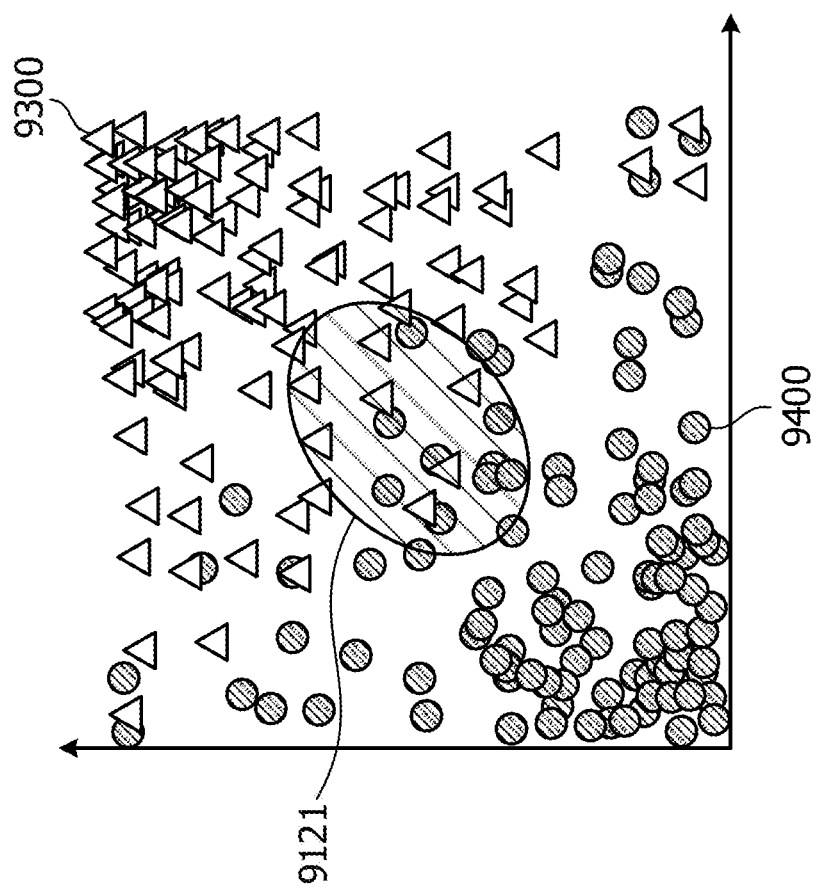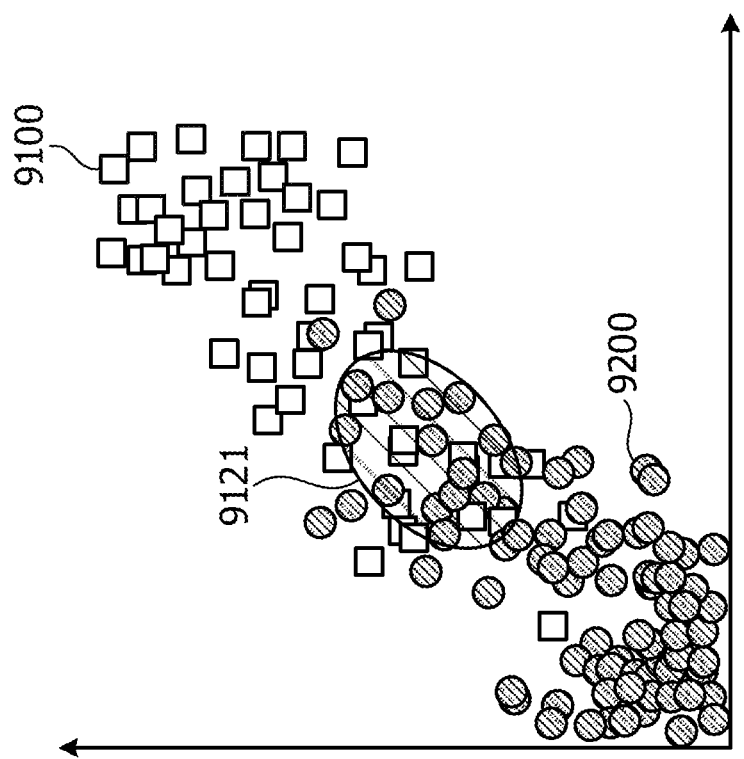

FIG. 10

| DETERMINATION TIME | MEAL | HEART RATE EVALUATION VALUE | ARM MOTION EVALUATION VALUE |
|---|---|---|---|
| 15:00 | ABSENCE | 0.12 | 0.05 |
| 15:01 | PRESENCE | 0.21 | 0.28 |
| 15:02 | PRESENCE | 0.28 | 0.35 |
| 15:03 | PRESENCE | 0.35 | 0.26 |
| ... | ... | | |

| DETERMINATION TIME | MEAL | CLASSIFICATION | CONTENT | HEART RATE EVALUATION VALUE | ARM MOTION EVALUATION VALUE |
|---|---|---|---|---|---|
| 15:00 | ABSENCE | - | - | 0.12 | 0.05 |
| 15:01 | PRESENCE | CONFECTIONARY | CHOCOLATE | 0.21 | 0.28 |
| 15:02 | PRESENCE | CONFECTIONARY | CHOCOLATE | 0.28 | 0.35 |
| 15:03 | PRESENCE | CONFECTIONARY | CHOCOLATE | 0.35 | 0.26 |
| ... | | | | | |
| 19:00 | PRESENCE | STAPLE FOOD | NOODLES | ... | ... |
| 19:01 | PRESENCE | STAPLE FOOD | NOODLES | ... | ... |
| 19:02 | ABSENCE | - | - | | |
| ... | | | | | |

MEAL DETECTION METHOD, MEAL DETECTION SYSTEM, AND STORAGE MEDIUM

CROSS-REFERENCE TO RELATED APPLICATION

This application is based upon and claims the benefit of priority of the prior Japanese Patent Application No. 2017-123739, filed on Jun. 23, 2017, the entire contents of which are incorporated herein by reference.

FIELD

The embodiments discussed herein are related to a meal detection method, a meal detection system, and a storage medium.

BACKGROUND

A technique for determining an eating action of a user by detecting the number of heartbeats or movement of the arm of a user, and the like with a sensor is known. For example, there is known a technique in which acceleration of three axes that are at least orthogonal to each other is detected with an acceleration sensor worn on lower arm parts of both arms of the user and the detected sensor signal is compared with a stored eating action determination criterion to thereby determine the presence or absence of the user's eating action.

There is also known a technique in which time-series data relating to the number of heartbeats is acquired and a feature amount relating to a second peak which appears subsequent to a first peak in which a peak of the number of heartbeats appears first after the start of a meal is calculated for each partial data included in the time-series data. In the technique, the presence or absence of meal is determined in the partial data by using the feature amount relating to the second peak calculated for each piece of partial data, and a meal time is estimated from the partial data determined to include the meal. Furthermore, there is also known a technique in which a feature amount indexed by the degree of similarity with a characteristic of heart rate change that appears at the end of the meal is calculated from time-series data of the number of heartbeats and the meal time is estimated from the feature amount. Japanese Laid-open Patent Publication No. 2011-115508, International Publication Pamphlet No. WO 2016/092707, International Publication Pamphlet No. WO 2016/143074, and the like are examples of the related art.

However, in the technique described above, even when the user is eating a meal, the meal may not be detected in a case where the movement of the arm is small or a case where a change in the heart rate is small. For example, in a case where the user wears a sensor on the dominant arm, when the user brings food to the mouth with the arm opposite to the dominant arm, the movement of the user's arm acquired by the sensor may be small. In a case where the amount of food to be brought to the mouth at once is significantly small, the change in the number of heartbeats of the user may be small. In the technique described above, it may not be detected that the user is eating a meal in such a case. In view of the matters described above, it is desirable to be able to detect a meal by the user.

As one aspect of the embodiment, provided are a meal detection program, a meal detection method, and a meal detection system for being able to detect a meal by a user.

SUMMARY

According to an aspect of the invention, A meal detection method executed by a processor of a computer, the meal detection method includes acquiring first sensing data from a first sensor configured to detect a motion of an arm of a target person; acquiring second sensing data from a second sensor configured to detect a heart rate of the target person; calculating a first evaluation value indicating likelihood that a meal is performed based on a first feature amount extracted from the first sensing data; calculating a second evaluation value indicating likelihood that the meal is performed based on a second feature amount extracted from the second sensing data; and determining whether the target person has eaten the meal or not, based on the first evaluation value and the second evaluation value.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIGS. 6A and 6B are diagrams illustrating other examples of the correspondence relationship between the heart rate, and the arm motion, and the action;

FIG. 10 is a diagram illustrating an example of teacher data in Example 2;

FIG. 14 is a diagram illustrating an example of teacher data in Example 3; and

DESCRIPTION OF EMBODIMENTS

Figure 1:
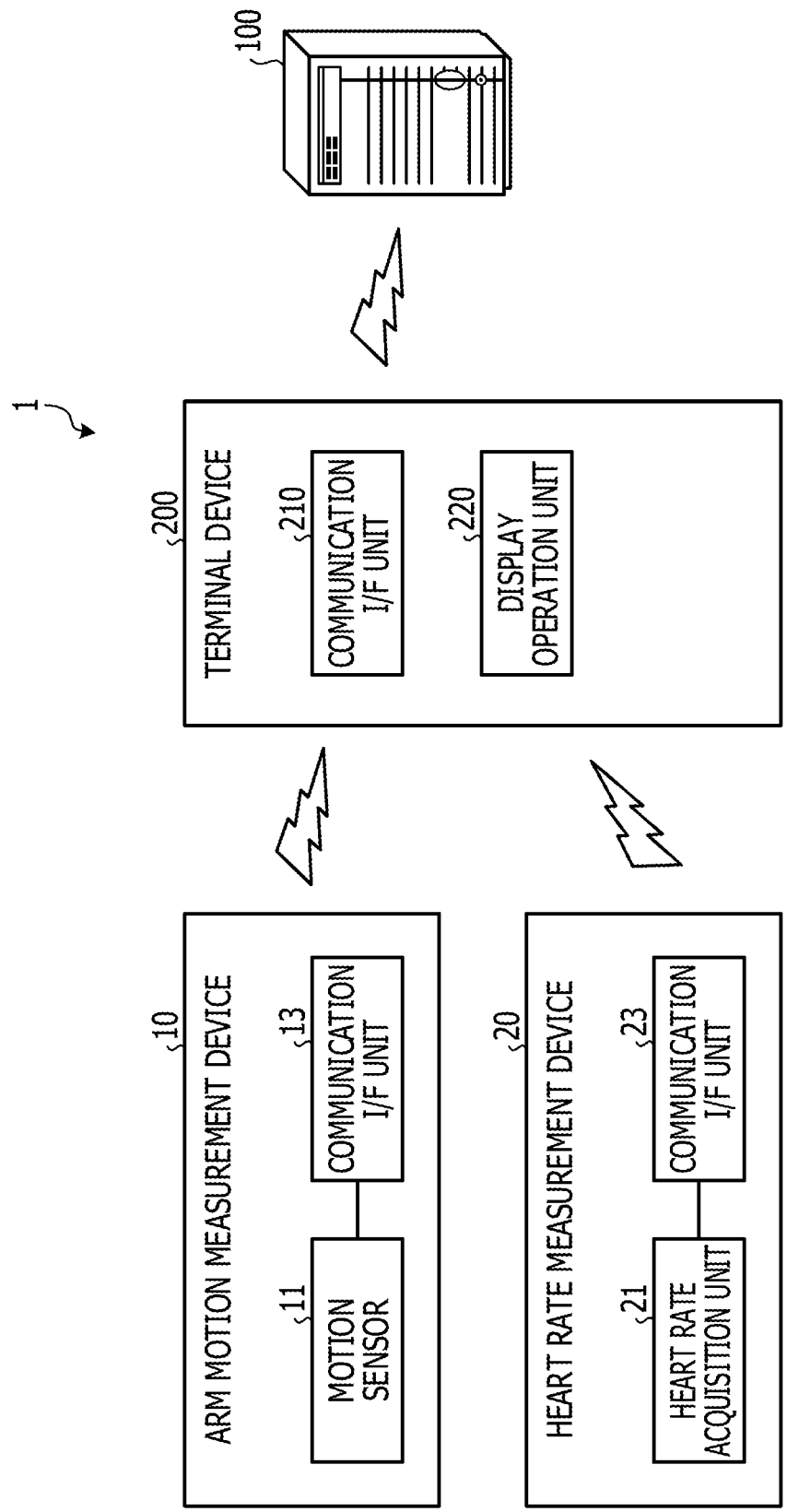
FIG. 1 is a diagram illustrating an example of a system configuration in Example 1.

In the following, embodiments of a meal detection program, a meal detection method, and a meal detection system disclosed in the present specification will be described in detail with reference to the drawings. The present disclosure is not limited by the embodiments. Each of the embodiments described below may be appropriately combined within a range that does not cause inconsistency. In the following embodiments, the same reference numerals are given to the same portions as those illustrated in the drawings described previously, and redundant description thereof will be omitted.

Example 1

System Configuration

A detection system according to Example 1 will be described with reference to FIG. 1. FIG. 1 is a diagram illustrating an example of a system configuration in Example 1. A detection system 1 illustrated in FIG. 1 includes an arm motion measurement device 10, a heart rate measurement device 20, a detection device 100, and a terminal device 200. The configuration of the detection device 100 will be described in detail later.

In Example 1, the detection device 100, the terminal device 200, and the arm motion measurement device 10, the heart rate measurement device 20, and the terminal device 200 are communicably connected with each other via a wireless or wired network. As a form of such a network, any type of communication network such as mobile communication such as a mobile phone, the Internet, local area network (LAN) or virtual private network (VPN) may be adopted, regardless of wired or wireless communication connection. In FIG. 1, a case where the arm motion measurement device 10, the heart rate measurement device 20, and the terminal device 200 are respectively one is illustrated. However, a plurality of arm motion measurement devices 10, heart rate measurement devices 20, and terminal devices 200 may be accommodated in the detecting system 1.

The arm motion measurement device 10 illustrated in FIG. 1 is, for example, a wrist band type measurement device, and is worn on a dominant arm or the like of a target person. For example, the arm motion measurement device 10 measures the movement of the arm of the target person at a predetermined sampling period by using a motion sensor 11 that detects accelerations of three axes orthogonal to each other. The arm motion measurement device 10 transmits data relating to the measured movement of the arm to the terminal device 200 by a communication interface (I/F) unit 13. The arm motion measurement device 10 is an example of a first sensor. Data relating to the movement of the arm is an example of first sensing data.

With this, the arm motion measurement device 10 acquires time-series data of accelerations in the up, down, left, right, front, and rear directions, which are sensed by the motion sensor 11 for each sampling point, as acceleration data. For such acceleration data, for example, data with which items such as time and acceleration are associated may be adopted. Similar to heart rate data described above, the term "time" herein may be the system time locally managed on the arm motion measurement device 10, for example, the elapsed time from any start point in time. Otherwise, the "time" may be the time expressed on a calendar such as a year, month, day, hour, minute, and second. The term "acceleration" may include three axes of accelerations in the up-and-down direction, the left-and-right direction, and the front-and-rear direction. For example, in a case where accelerations are narrowed to accelerations in a portion of the directions among accelerations of the three axes and are used for the detection device 100, acceleration in the direction not used by the detection device 100 may also be removed from acceleration data.

In the heart rate measurement device 20 illustrated in FIG. 1, a wearable heart rate sensor to be worn on a living body part of a user, for example, a chest, an arm, a wrist, or the like, may be adopted as a heart rate acquisition unit 21. For example, a pulse by a photoelectric pulse wave sensor may also be adopted. The heart rate measurement device 20 transmits data relating to the heart rate measured by the heart rate acquisition unit 21 to the terminal device 200 by the communication I/F unit 23. The heart rate measurement device 20 is an example of a second sensor. Data relating to the heart rate is an example of second sensing data.

The terminal device 200 illustrated in FIG. 1 is used by, for example, a target person who wears the arm motion measurement device 10 and the heart rate measurement device 20. The terminal device 200 is a portable computer such as a smartphone, a tablet, a laptop computer, or the like. But, the terminal device 200 is not limited the portable computer and may be a stationary computer or the like.

The terminal device 200 receives data relating to the motion of the arm and data relating to the heart rate from the arm motion measurement device 10 and the heart rate measurement device 20 through the communication I/F unit 210, and transmits the received data to the detection device 100. The terminal device 200 receives information on a meal determination result from the detection device 100 and causes a display operation unit 220 to display the information.

The detection device 100 illustrated in FIG. 1 detects whether the target person is eating a meal or not, by using data relating to the motion of the arm and data relating to the heart rate received from the terminal device 200. The detection device 100 determines how similar the change in the heart rate of the target person is to a pattern of the heart rate that occurs when eating a meal. The detection device 100 determines how much the motion of the target person's arm is similar to the pattern of the movement of the arm that occurs when the target person is eating a meal, for example. Then, in a case where an evaluation value indicating the degree of similarity with the pattern satisfies the predetermined condition, the detection device 100 determines that the target person is eating a meal. The evaluation value in Example 1 takes a value between 0 and 1, for example. As the evaluation value is closer to 1, the evaluation value indicates that the specified heart rate or arm motion is similar to the pattern when the target person is eating a meal.

Figure 2:
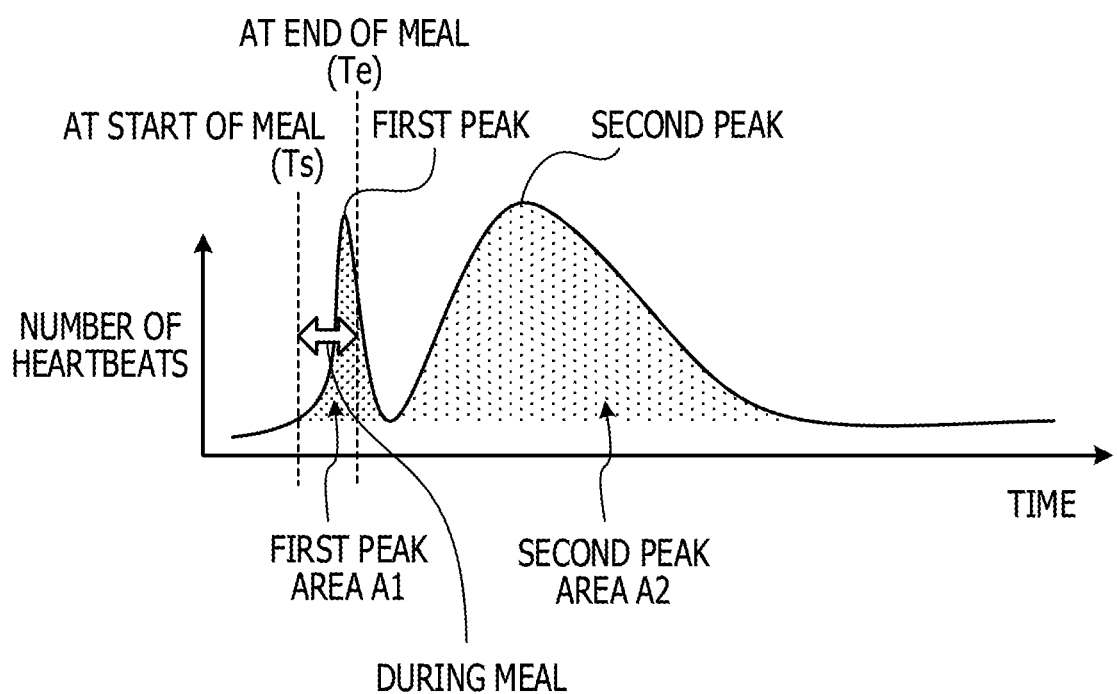
FIG. 2 is a diagram illustrating an example of a pattern of the heart rate change at the time of a meal.

In the heart rate in a case of eating a meal, the second peak appears after the first peak appears, and the second peak tends to extend over a long period of time than the first peak. FIG. 2 is a diagram illustrating an example of a pattern of the heart rate change at the time of a meal. In FIG. 2, as an example, changes in the heart rate before and after the start of a meal are represented in a graph. The vertical axis illustrated in FIG. 2 indicates the number of heartbeats per unit time. The horizontal axis indicates the elapsed time (time) from immediately before the start of the meal.

As illustrated in FIG. 2, two peaks in which the number of heartbeats rises (increases) and turns to fall (decrease) with the lapse of time exist in the change in the number of heartbeats, which occurs after the meal starts, accompanying the meal. That is, with the lapse of time from the meal starting time Ts, a "first peak" which is a peak of the change in the number of heartbeats appearing ahead of the meal after the start of the meal and a "second peak" which is a peak of the change in the number of heartbeats appearing following the first peak appear. In the following, a predetermined area including a waveform of a portion of the first peak may be referred to as a "first peak area A1". A predetermined area including a waveform of a portion of the second peak may be referred to as a "second peak area A2".

Among the first and second peaks, the "first peak" corresponds to a rise in the heart rate accompanying an eating action, for example, is estimated to be an increase in the number of heartbeats due to chewing or peristaltic movement of the esophagus. The "second peak" is estimated to be an increase in the number of heartbeats due to digestive activity in digestive organs (gastrointestinal and the like) for ingested substances, that is, food and the like, ingested by the eating action, for example.

The detection device 100 in Example 1 calculates the degree of similarity between a first feature amount calculated from the acquired data relating to the heart rate and the pattern of the heart rate that occurs when eating a meal as illustrated in FIG. 2 as an evaluation value relating to the heart rate. The evaluation value on the heart rate is an example of a second evaluation value.

Similarly, as for the movement of the arm occurring when eating a meal, a definite pattern may be generated similarly to the pattern of the heart rate as illustrated in FIG. 2. For example, the number of times that a motion of raising and lowering the arm, which is specified from the acquired data relating to the motion of the arm, occurs within a predetermined time may be used as a feature amount relating to the movement of the arm. The detection device 100 in Example 1 calculates the degree of similarity between the second feature amount calculated from the acquired data relating to the movement of the arm and the pattern of the movement of the arm that occurs when eating a meal, as an evaluation value relating to the motion of the arm. The evaluation value relating to the movement of the arm is an example of a first evaluation value.

Then, the detection device 100 in Example 1 determines that the target person is eating a meal in a case where the evaluation value relating to the movement of the arm and the evaluation value relating to the change in the heart rate satisfy a predetermined condition. In the following, determining that the target person is eating a meal may be referred to as the expression "determining it as a meal". In the following, matters that the target person is not eating a meal may be simply referred to as the "non-meal".

Figure 3:
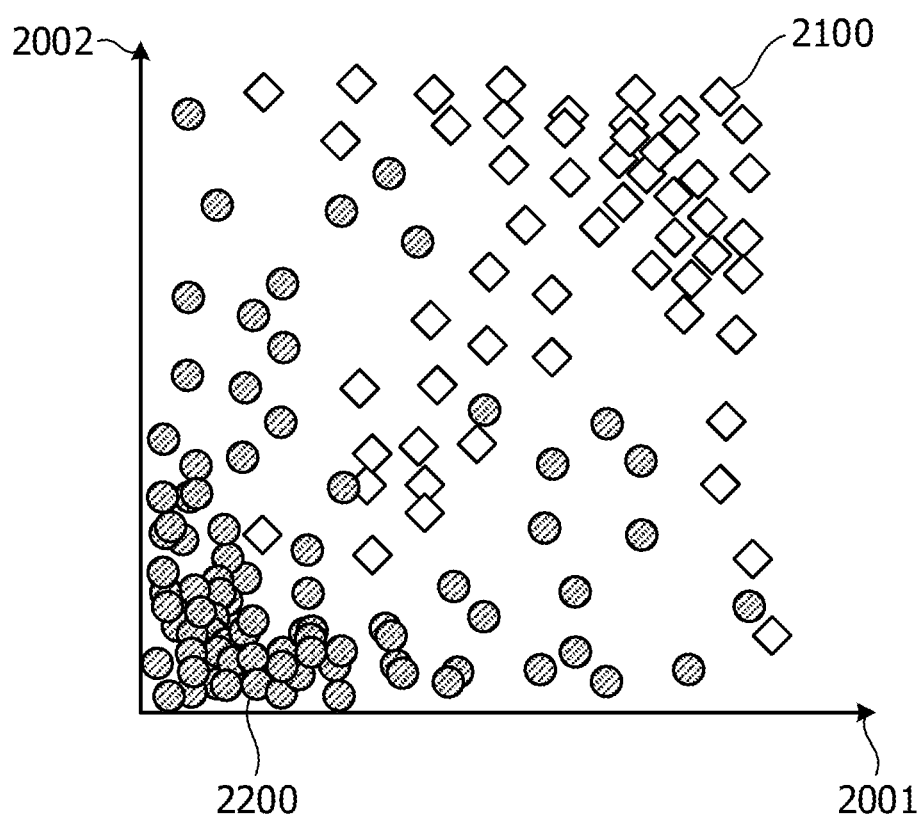
FIG. 3 is a diagram illustrating an example of a correspondence relationship between a heart rate, an arm motion, and an action.

When plotting of the correspondence relationship between the evaluation value relating to the movement of the arm and the evaluation value relating to the change in the heart rate of the target person at a specific point in time and whether or not the target person is eating a meal at the specific point in time is made, for example, a graph as illustrated in FIG. 3 is obtained. FIG. 3 is a diagram illustrating an example of a correspondence relationship between a heart rate, an arm motion, and an action. A vertical axis 2002 illustrated in FIG. 3 indicates the evaluation value relating to the change in the heart rate. A horizontal axis 2001 indicates the evaluation value relating to the movement of the arm. A marker 2100 indicates data at the time of a meal. A marker 2200 indicates data relating to actions other than the meal.

Meanwhile, when it is attempted to reduce detection failure at the time of detecting a meal, erroneous detection, by which determining that the motion corresponds to a meal is made even for data during actions other than the meal, increases. On the other hand, when it is attempted to suppress erroneous detection, there is a concern that detection failure that it is not detected as a meal even for data at the time of the meal increases.

Figure 4A:
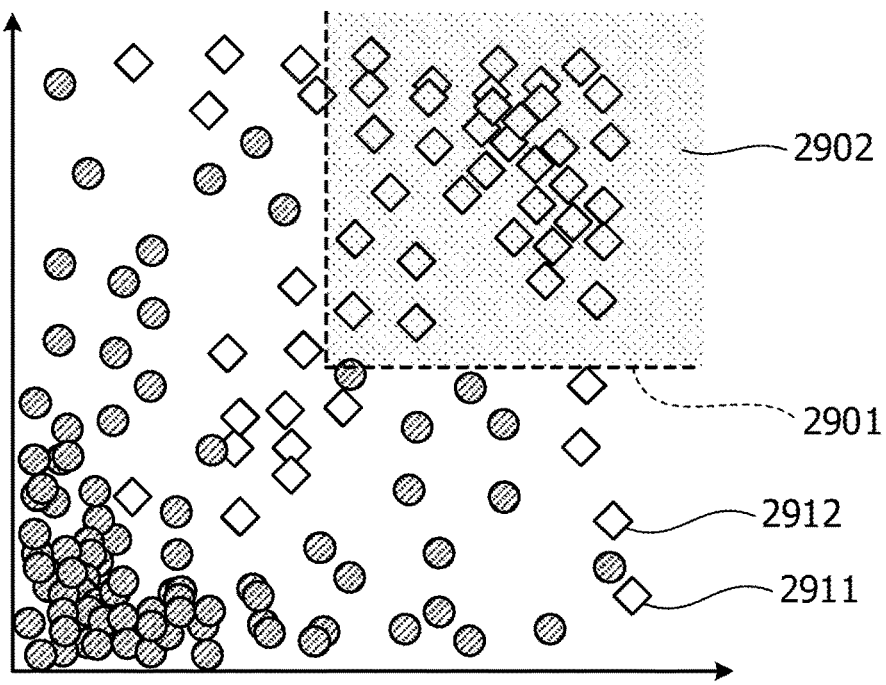
FIG. 4A is a diagram illustrating an example of a meal determination result.

FIG. 4A is a diagram illustrating an example of a meal determination result. In the example illustrated in FIG. 4A, only when both the evaluation value of the motion of the arm represented on the vertical axis and the evaluation value of the heart rate represented on the horizontal axis are equal to or greater than a predetermined threshold value 2901, it is determined that the target person is eating a meal. That is, it is determined that data included in an area 2902 is data at the time of the meal and the other data is data at the time of the action other than the meal.

In the example illustrated in FIG. 4A, the possibility that the action other than the meal is erroneously detected as the meal is reduced. On the other hand, as in a case of data 2911 and 2912, the possibility of detection failure increases.

Figure 4B:
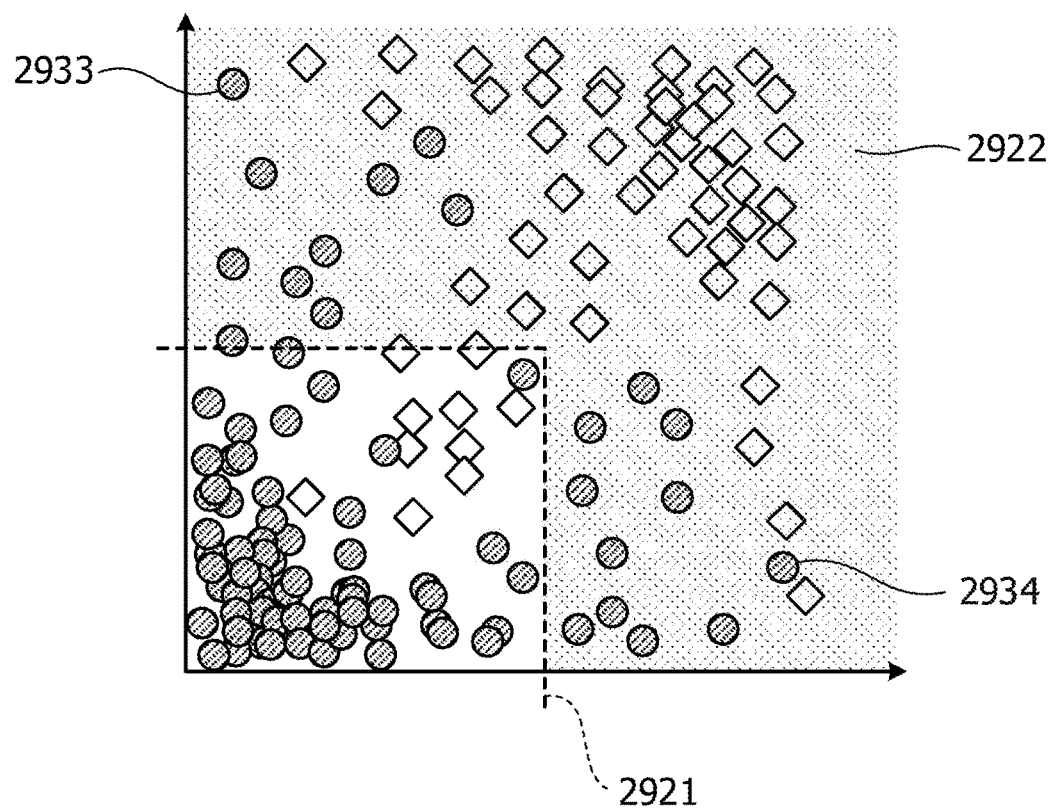
FIG. 4B is a diagram illustrating another example of the meal determination result.

Next, FIG. 4B is a diagram illustrating another example of the meal determination result. In the example illustrated in FIG. 4B, in a case where at least one of the evaluation value of the motion of the arm represented on the vertical axis and the evaluation value of the heart rate represented on the horizontal axis is equal to or greater than a predetermined threshold value 2921, it is determined that the target person is eating a meal. That is, it is determined that data included in an area 2922 is data at the time of the meal and the other data is data at the time of the action other than the meal.

In the example illustrated in FIG. 4B, the possibility that data at the time of the meal is not detected as a meal decreases. On the other hand, as in the case of data 2933 and 2934, the possibility that the action other than the meal is erroneously detected as the meal increases.

On the other hand, in Example 1, the detection device 100 determines that, for example, data at the point in time when only one of the heart rate evaluation value and the arm motion evaluation value is high and data at the point in time when the heart rate evaluation value and the arm motion evaluation value become similar values are data at the time of the meal. For example, in a case where a difference between the heart rate evaluation value and the arm motion evaluation value is equal to or less than the first threshold value and an average value of the heart rate evaluation value and the arm motion evaluation value is equal to or greater than the second threshold value, it is determined that the target person has eaten the meal. The detection device 100 may determine that the target person has eaten the meal in a case where one of the heart rate evaluation value and the arm motion evaluation value is equal to or greater than a third threshold value. The third threshold value is, for example, a value greater than the second threshold value.

For example, in a case where the average value of the heart rate evaluation value and the arm motion evaluation value at a certain point in time is 0.6 or more, the detection device 100 determines that the point in time corresponds to a case of eating a meal. The detection device 100 determines that the point in time corresponds to a meal even in a case of being fallen within an area in which the average value of the average value of the heart rate evaluation value and the arm motion evaluation value at a certain point in time is 0.2 or more and an absolute value of the difference between the arm motion evaluation value and the heart rate evaluation value is less than 0.1, it is also determined that the point in time corresponds to a meal.

Figure 5:
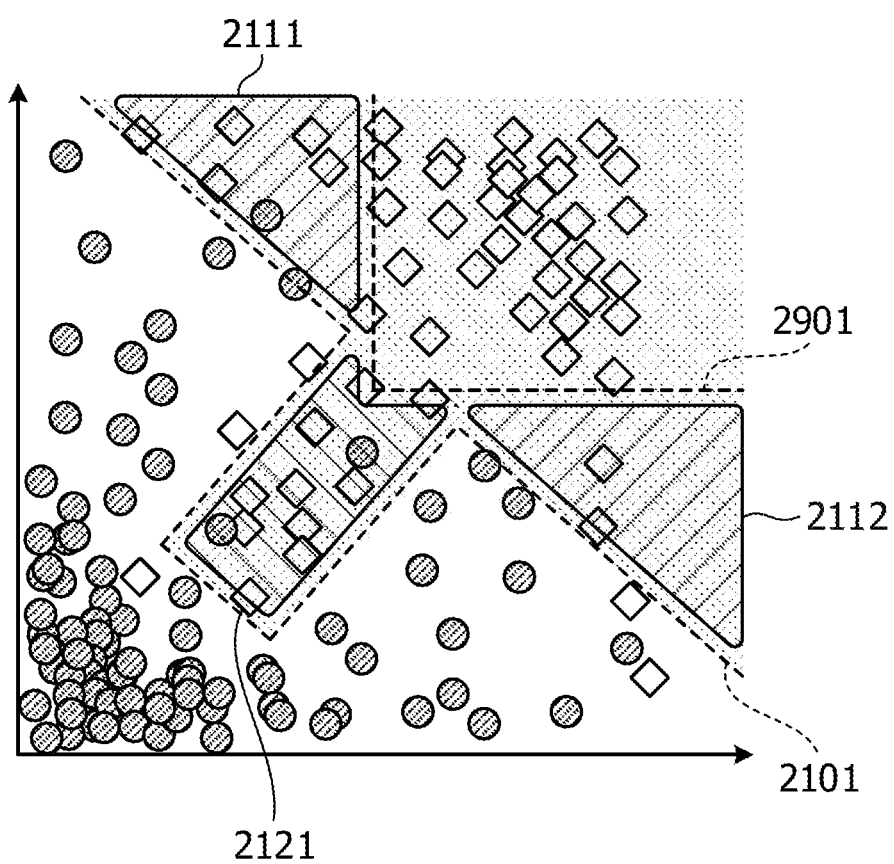
FIG. 5 is a diagram illustrating an example of a meal determination result in Example 1.

The result of a meal determination process using the heart rate evaluation value and the arm motion evaluation value in Example 1 will be described with reference to FIG. 5. FIG. 5 is a diagram illustrating an example of the meal determination result in Example 1. As illustrated in FIG. 5, in the meal determination result in Example 1, in addition to data included in the area 2902 illustrated in FIG. 4A, data of which the average value of the heart rate evaluation value and the arm motion evaluation value is equal to or greater than a threshold value 2101, for example, 0.6 or more and which is included in areas 2111 and 2112 is also determined as a meal. The threshold value 2101 is an example of the first threshold value.

Furthermore, in FIG. 5, data of which the average value of the heart rate evaluation value and the arm motion evaluation value is equal to or greater than the second threshold value, for example, 0.2 or more and which is included in an area 2121 and the absolute value of the difference between the heart rate evaluation value and the arm motion evaluation value is less than the third threshold value, for example less than 0.1 is also determined as a meal.

With the configuration as described above, in Example 1, it is possible to further suppress detection failure than the meal determination result illustrated in FIG. 4A and to further suppress erroneous detection than the meal determination result illustrated in FIG. 4B.

The reason that the meal may be accurately detected in Example 1 is because the action of the meal has two properties as follows.

As a first property, the cause of erroneous detection when detecting a meal is different between the case of meal detection using the characteristic of change in the number of heartbeats and the case of meal detection using the characteristic of arm motion. For example, in a case where the change in the heart rate of the target person is similar to the pattern of the heart rate that occurs when eating a meal depending on mental tension or change in the external environment, the evaluation value relating to the change in the heart rate becomes higher. In this case, when the threshold value for the evaluation value relating to the change in the heart rate is set low, there is a concern that erroneous detection occurs at the time of meal detection.

However, in this case, there is little possibility that the motion of the arm is similar to the pattern of the motion occurring when eating a meal, for example, the movement that brings the hands closer to the face, is low. That is, even in a case where the evaluation value relating to the change in the heart rate increases due to factors other than the meal, the change in the heart rate does not occur in conjunction with the motion of the arm occurring in the case of eating a meal.

For that reason, even in a case where erroneous detection occurs based on the evaluation value relating to the change in the heart rate, there is little possibility that erroneous detection based on the characteristic of the movement of the arm occurs at the same time. Similarly, even in the case where the motion of the arm is similar to the pattern of the motion occurring when eating a meal, such as scratching of the face by the target person, and erroneous detection based on the characteristic of the motion of the arm occurs, there is little possibility that erroneous detection based on the characteristic of changes in heart rate occurs simultaneously.

As a second property, in the case of the meal, there is a relationship between the characteristic of the motion of the arm and the characteristic of heart rate change in many cases. For example, in a case where the amount of meal is small, the number of movements of bringing the arm closer to the face is small and the heart rate change is also often small. That is, in a case where the motion of the arm is smaller than the motion in a normal meal, the change in the heart rate is often small.

On the other hand, in actions other than the meal, at least one of the first and second properties described above is often not satisfied in many cases. FIGS. 6A and 6B are diagrams illustrating another example of the correspondence relationship between the heart rate, the arm motion, and the action. FIG. 6A illustrates a correspondence relationship between the heart rate change and the arm motion in an action 9100 not satisfying the first property and an action 9200 other than the action 9100. FIG. 6B illustrates a correspondence relationship between the heart rate change and the arm motion in an action 9300 not satisfying the second property and an action 9400 other than the action 9300.

As illustrated in FIG. 6A, in an area 9121 in which the average value of the heart rate evaluation value and the arm motion evaluation value is somewhat high and the arm motion evaluation value and the heart rate evaluation value are close to each other, the actions 9100 and 9200 are mixed. Similarly, as illustrated in FIG. 6B, in the area 9121 in which the average value of the heart rate evaluation value and the arm motion evaluation value is somewhat high and the arm motion evaluation value and the heart rate evaluation value are close to each other, the actions 9300 and 9400 are mixed. In such a case, in the meal determination result in Example 1, there is a high possibility that erroneous detection in the area 9121 may increase.

In a case where the average value of the heart rate evaluation value and the arm motion evaluation value, which are included in the area 2121 of FIG. 5, is somewhat high and the arm motion evaluation value and the heart rate evaluation value are close to each other, it is possible to accurately detect a meal according to the first property and the second property as described above.

For example, when the target person eats beans one by one, the motion of the arm seems to be that for a meal, but the heart rate is hard to react because the amount of beans at every bite is small. For example, when the target person has eaten a meal with a hand opposite to the hand wearing the sensor, reaction of the heart rate is close to that of the normal meal, but the motion of the arm is not a meal-like action. In such a case, one of the heart rate evaluation value and the arm motion evaluation value becomes higher and thus, the heart rate evaluation value and the arm motion evaluation value are included in the area 2111 or 2112 in FIG. 5.

As described above, in a case where at least one of the evaluation value based on the movement of the arm and the evaluation value based on the heart rate is high, or a case where both the evaluation values are intermediate and have similar values, the detection device in Example 1 determines that the target person has eaten a meal and thus, it is possible to accurately detect the meal.

Functional Block

Figure 7:
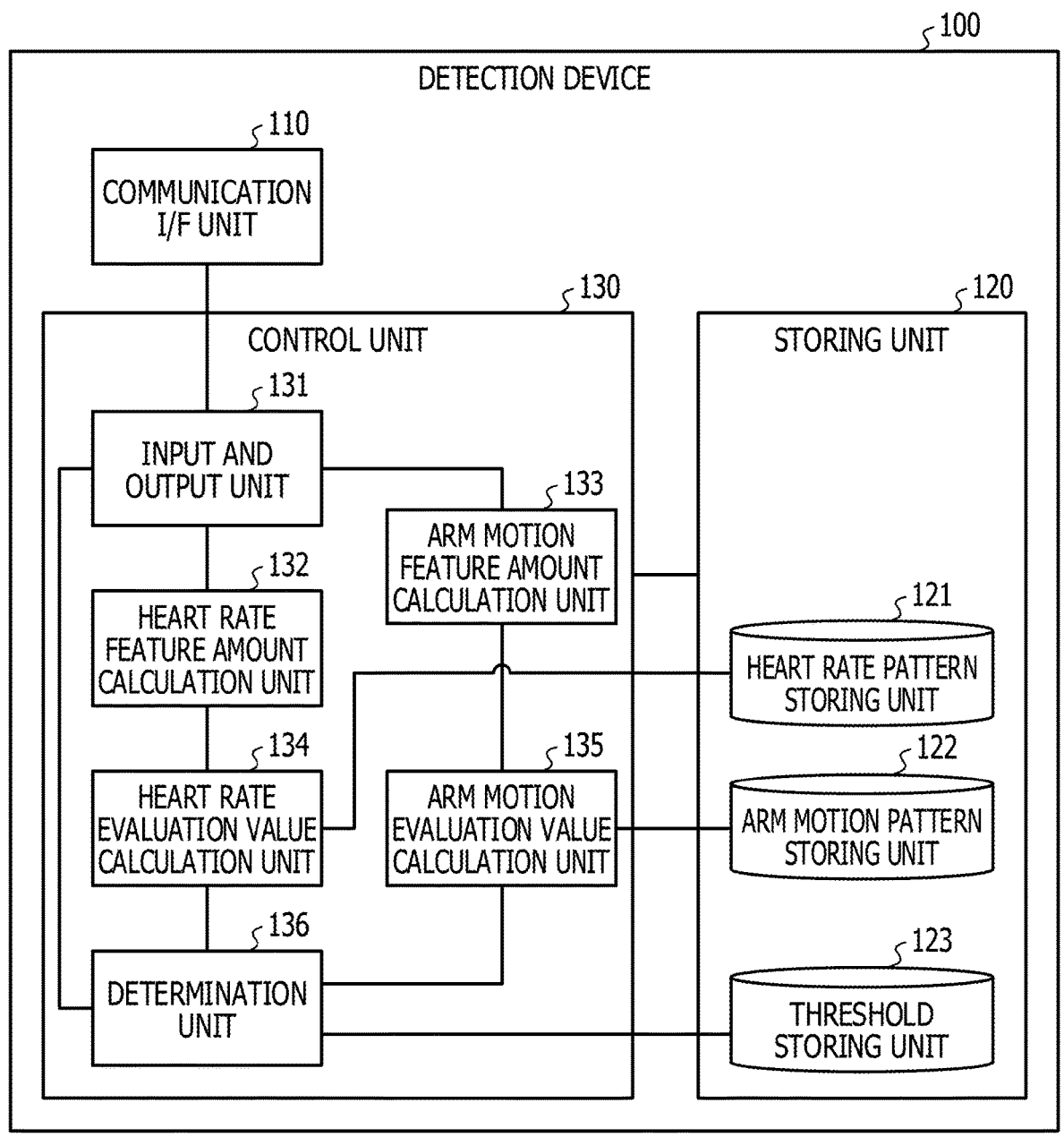
FIG. 7 is a diagram illustrating an example of a functional configuration of a detection device in Example 1.

Next, the detection device 100 in Example 1 will be described with reference to FIG. 7. FIG. 7 is a diagram illustrating an example of a functional configuration of a detection device in Example 1. The detection device 100 illustrated in FIG. 7 includes a communication I/F unit 110, a storing unit 120, and a control unit 130. The detection device 100 in Example 1 is, for example, a computer such as a server computer that receives a processing request from the terminal device 200, but is not limited thereto. The detection device 100 may be a stand-alone type computer such as a personal computer. Otherwise, the detection device 100 may be a portable computer such as a smartphone, a tablet, or a notebook computer.

The communication I/F unit 110 controls communication with another computer, such as the terminal device 200, regardless of wired or wireless communication connection. The communication I/F unit 110 is a communication interface such as a network interface card (NIC) or the like.

The storing unit 120 stores, for example, a program executed by the control unit 130, various data, and the like. The storing unit 120 includes a heart rate pattern storing unit 121, an arm motion pattern storing unit 122, and a threshold value storing unit 123. The storing unit 120 corresponds to a semiconductor memory device such as a random access memory (RAM), a read only memory (ROM), a flash memory, or a storage device such as a hard disk drive (HDD).

The heart rate pattern storing unit 121 stores, for example, a pattern of the heart rate change at the time of a meal as illustrated in FIG. 2. The pattern of the heart rate change is acquired from an external computer through the communication I/F unit 110 and the input and output unit 131, for example.

The arm motion pattern storing unit 122 stores a pattern of the movement of the arm at the time of the meal. In the pattern of the motion of the arm, for example, the number of times of raising and lowering the arm within a predetermined time is stored. The pattern of the movement of the arm is acquired from an external computer through the communication I/F unit 110 and the input and output unit 131, for example, similarly to the pattern of the heart rate change.

The threshold value storing unit 123 stores a threshold value for determining whether the evaluation value corresponds to a meal or not. The threshold value is input by an administrator of the detection device 100 (not illustrated), for example. However, the threshold value storing unit is not limited thereto, and may be configured to be updated by a heart rate evaluation value calculation unit 134 and the arm motion evaluation value calculation unit 135.

The control unit 130 is a processing unit that controls overall processing of the detection device 100. The control unit 130 is realized, for example, in such a way that a program stored in an internal storage device is executed by a central processing unit (CPU), a micro processing unit (MPU), or the like by using the RAM as a work area. For example, the control unit 130 may be realized by an integrated circuit such as an application specific integrated circuit (ASIC), a field programmable gate array (FPGA), or the like.

The control unit 130 includes the input and output unit 131, a heart rate feature amount calculation unit 132, an arm motion feature amount calculation unit 133, the heart rate evaluation value calculation unit 134, the arm motion evaluation value calculation unit 135, and a determination unit 136. The input and output unit 131, the heart rate feature amount calculation unit 132, the arm motion feature amount calculation unit 133, the heart rate evaluation value calculation unit 134, the arm motion evaluation value calculation unit 135, and the determination unit 136 are examples of an electronic circuit included in the processor and examples of a process to be executed by the processor.

The input and output unit 131 inputs and outputs information to and from the terminal device 200 through the communication I/F unit 110. The input and output unit 131 receives an instruction to start a meal detection process from another computer such as the terminal device 200. The input and output unit 131 receives data relating to the motion of the arm and data relating to the heart rate from the terminal device 200, and outputs the data to the heart rate feature amount calculation unit 132 and the arm motion feature amount calculation unit 133. The input and output unit 131 outputs the meal determination result by the determination unit 136 to another computer such as the terminal device 200. The input and output unit 131 is an example of a first acquisition unit and a second acquisition unit.

The heart rate feature amount calculation unit 132 calculates the heart rate feature amount using data relating to the heart rate output from the input and output unit 131. For example, the heart rate feature amount calculation unit 132 sets a "window" having a predetermined time width having a starting end a predetermined time before the time for determining whether it is a meal or an terminating end the predetermined time after the time for determining whether it is a meal, and calculates a heart rate feature amount within the window. In the following, the time for determining whether it is a meal may be referred to as the "determination time".

The heart rate feature amount calculation unit 132 repeats acquiring data relating to the heart rate from the input and output unit 131 until data relating to the heart rate for a period satisfying the window width is acquired. Then, while moving the determination time sequentially backward, the heart rate feature amount calculation unit 132 calculates the heart rate feature amount within the window corresponding to each determination time by using the acquired data relating to the heart rate. The heart rate feature amount calculation unit 132 outputs the calculated heart rate feature amount to the heart rate evaluation value calculation unit 134. The heart rate feature amount is, for example, the number of heartbeats every 10 minutes from the determination time to a predetermined time. In addition, for example, feature amounts such as amplitudes described in International Publication Pamphlet No. WO2016/092707, International Publication Pamphlet No. WO2016/143074 are calculated.

The arm motion feature amount calculation unit 133 calculates the arm motion feature amount using data relating to the motion of the arm output from the input and output unit 131. The arm motion feature amount calculation unit 133 repeats acquiring data relating to the motion of the arm from the input and output unit 131 until data relating to the movement of the arm for the period satisfying the window width is acquired. Then, while moving the determination time sequentially backward, the arm motion feature amount calculation unit 133 calculates the arm motion feature amount within the window corresponding to each determination time by using the acquired data relating to the motion of the arm. The arm motion feature amount calculation unit 133 outputs the calculated arm motion feature amount to the arm motion evaluation value calculation unit 135.

The heart rate evaluation value calculation unit 134 calculates a heart rate evaluation value using the heart rate feature amount acquired from the heart rate feature amount calculation unit 132. The heart rate evaluation value calculation unit 134 calculates, for example, the degree of similarity between the heart rate feature amount and the pattern of the heart rate change stored in the heart rate pattern storing unit 121 as the heart rate evaluation value, and outputs the heart rate evaluation value to the determination unit 136. The heart rate evaluation value calculation unit 134 is an example of a first calculation unit.

The arm motion evaluation value calculation unit 135 calculates the arm motion evaluation value using the arm motion feature amount acquired from the arm motion feature amount calculation unit 133. The arm motion evaluation value calculation unit 135 calculates, for example, the degree of similarity between the arm motion feature amount and the pattern of the arm motion stored in the arm motion pattern storing unit 122 as the arm motion evaluation value and outputs the arm motion evaluation value to the determination unit 136. The arm motion evaluation value calculation unit 135 is an example of a second calculation unit.

The determination unit 136 determines whether the determination time corresponds to a meal or not, by using the heart rate evaluation value and the arm motion evaluation value. For example, the determination unit 136 refers to the threshold value storing unit 123 and compares the average value of the heart rate evaluation value and the arm motion evaluation value or the difference therebetween with a predetermined threshold value. The determination unit 136 outputs the meal determination result to the terminal device 200 through the communication I/F unit 110, for example. The determination unit 136 is an example of a determination unit.

Flow of Process

Figure 8:
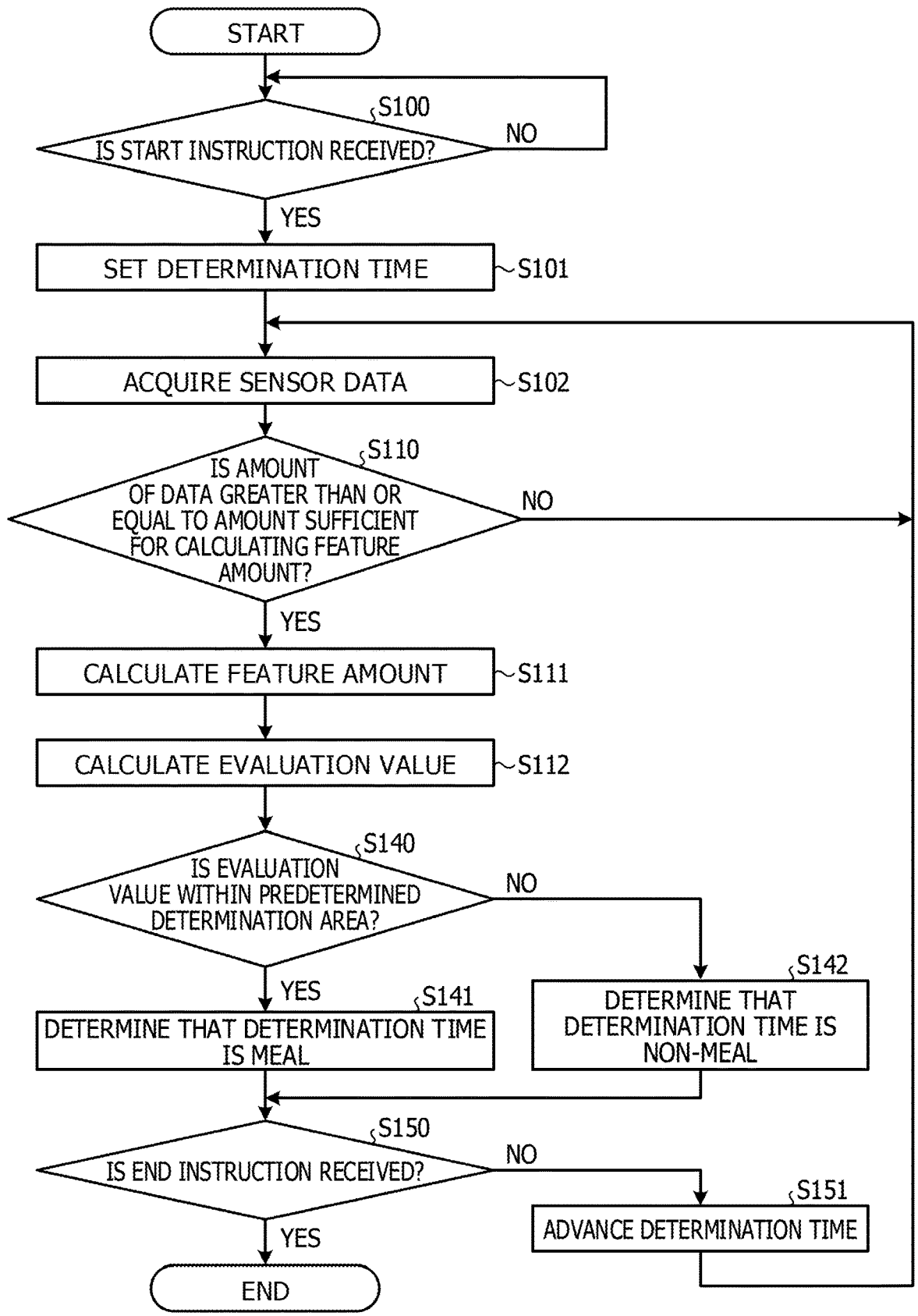
FIG. 8 is a flowchart illustrating an example of a detection process in Example 1.

Next, a process in Example 1 will be described with reference to FIG. 8. FIG. 8 is a flowchart illustrating an example of a detection process in Example 1. As illustrated in FIG. 8, the input and output unit 131 of the detection device 100 waits (No in S100) until a start instruction is received from the terminal device 200 or another computer through the communication I/F unit 110.

In a case where it is determined that the start instruction is received (Yes in S100), the input and output unit 131 sets the time to be a target for calculating the feature amount (S101). Next, the input and output unit 131 acquires sensor data relating to the motion of the arm and sensor data relating to change in the heart rate from the terminal device 200 through the communication I/F unit 110 (S102). Next, the heart rate feature amount calculation unit 132 determines whether an amount of sensor data sufficient for calculating the feature amount is obtained or not (S110). In a case where it is determined that a sufficient amount of sensor data is not obtained (No in S110), the heart rate feature amount calculation unit 132 returns to S102 and repeats the process.

On the other hand, in a case where it is determined that the sufficient amount of sensor data is obtained (Yes in S110), the heart rate feature amount calculation unit 132 calculates the heart rate feature amount using the sensor data. Similarly, the arm motion feature amount calculation unit 133 also calculates the arm motion feature amount using the sensor data (S111). Next, the heart rate evaluation value calculation unit 134 calculates the heart rate evaluation value using the calculated heart rate feature amount. Similarly, the arm motion evaluation value calculation unit 135 calculates the evaluation value of the arm motion using the calculated arm motion feature amount (S112).

Then, the determination unit 136 determines whether the calculated evaluation value is within a predetermined determination area or not (S140). In a case where the determination unit 136 determines that the evaluation value is within the predetermined determination area (Yes in S140), the determination unit 136 determines that the determination time is a meal (S141) and proceeds to S150. On the other hand, in a case where the determination unit 136 determines that the evaluation value is not within the predetermined determination area (No in S140), the determination unit 136 determines that the determination time is a non-meal (S142) and proceeds to S150.

Then, the input and output unit 131 determines whether an end instruction is received from the terminal device 200 or another computer through the communication I/F unit 110 or not (S150). In a case where it is determined that the end instruction is not received (No in S150), the input and output unit 131 advances the determination time (S151), and returns to S102 to repeat the process. On the other hand, in a case where it is determined that the end instruction is received (Yes in S150), the input and output unit 131 ends the process.

Effect

As described above, the detection device in Example 1 acquires first sensing data from the first sensor capable of detecting the motion of the arm of the target person and acquires second sensing data from the second sensor capable of detecting the motion of the arm of the target person. The detection device calculates a first evaluation value, which indicates the likelihood that a meal based on the movement of the arm is performed, from the first feature amount extracted from the first sensing data. The detection device calculates a second evaluation value, which indicates the likelihood that a meal based on the state of the heart rate is performed, from the second feature amount extracted from the second sensing data. Furthermore, the detection device determines whether the target person has eaten a meal or not, based on the first evaluation value and the second evaluation value. With this, it is possible to detect a meal even in a case where the motion of the arm during the meal is small or a case where the response of the heart rate is small. The detection device in Example 1 may reduce the burden of wearing the sensor by the target person compared to a configuration in which a sound collecting microphone is worn on the neck of the target person.

The detection device according to Example 1 may determine that the target person has eaten a meal in a case where the difference between the first evaluation value and the second evaluation value is equal to or less than a predetermined first threshold value. Furthermore, the detection device may determine that the target person has eaten a meal in a case where the first evaluation value and the second evaluation value are equal to or greater than a predetermined second threshold value. With this, it is possible to suppress erroneous detection in a case where a meal is detected by combining the motion of the arm and the change in the heart rate.

The detection device according to Example 1 may determine that the target person has eaten a meal in a case where one of the first evaluation value and the second evaluation value is equal to or greater than a predetermined third threshold value. With this, even in a case where one of the arm motion evaluation value and the heart rate evaluation value is less than the threshold value due to some cause, it is possible to suppress detection failure.

Example 2

In Example 1, whether the target person is eating a meal or not is determined by comparing the evaluation value relating to the motion of the arm and the evaluation value relating to the change in the heart rate with the first threshold value to the third threshold value, but the embodiments are not limited thereto. For example, a configuration in which the model generated by machine learning may be used to determine whether the target person is eating a meal or not may be adopted.

Accordingly, in Example 2, a configuration for detecting the meal of the target person based on the motion of the arm and the change in the heart rate using machine learning will be described. In Example 2, for example, an evaluation value vector which is a value obtained by summing the heart rate evaluation values or arm motion evaluation values calculated for each piece of time-series data is used as information indicating the motion of the arm and the change in the heart rate.

For machine learning, algorithms such as deep learning, support vector machine (SVM), decision tree, random forest, nearest neighbor may be used. The model used in machine learning is generated from data obtained by, for example, further linking information on whether a meal is actually performed at each determination time or not with the arm motion evaluation value and the heart rate evaluation value at each determination time.

Functional Block

Figure 9:
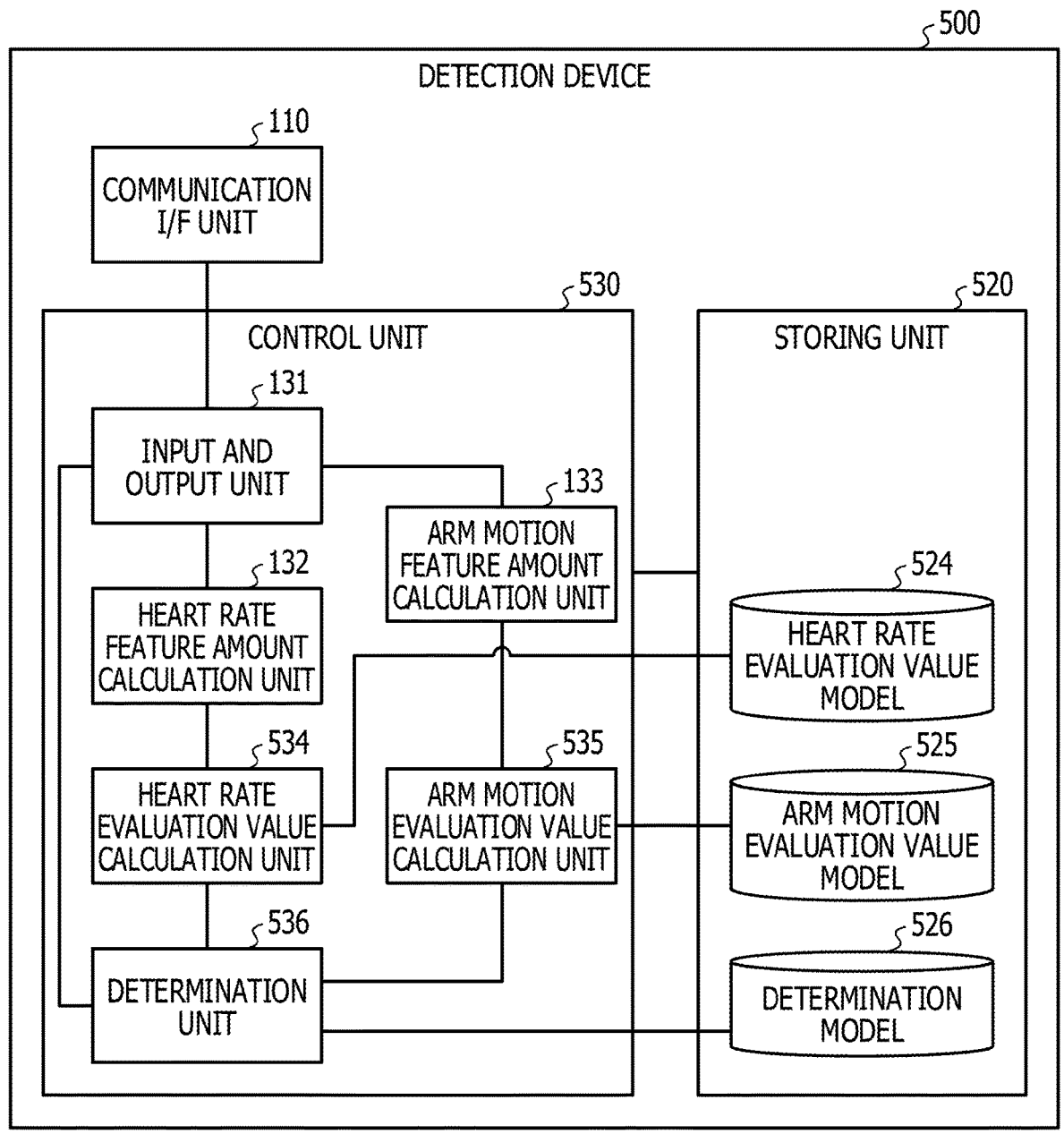
FIG. 9 is a diagram illustrating an example of a functional configuration of a detection device in Example 2.

A detection device 500 in Example 2 will be described with reference to FIG. 9. FIG. 9 is a diagram illustrating an example of a functional configuration of a detection device in Example 2. The detection device 500 illustrated in FIG. 9 includes the communication I/F unit 110, a storing unit 520, and a control unit 530.

The storing unit 520 stores, for example, a program to be executed by the control unit 530, various data, and the like. The storing unit 520 includes a heart rate evaluation value model 524, an arm motion evaluation value model 525, and a determination model 526. The storing unit 520 corresponds to a semiconductor memory element such as a RAM, a ROM, a flash memory, or a storage device such as an HDD.

The heart rate evaluation value model 524 is a learning model used when the heart rate evaluation value is calculated from the heart rate feature amount. The heart rate evaluation value model 524 is generated using previously known information, for example, the correspondence relationship between the heart rate feature amount and the heart rate evaluation value at the determination time. The heart rate evaluation value model 524 is generated by the heart rate evaluation value calculation unit 534 or is updated each time teacher data is acquired, for example.

The arm motion evaluation value model 525 is a learning model used for calculating the arm motion evaluation value from the arm motion feature amount. The arm motion evaluation value model 525 is generated using previously known information, for example, the correspondence relationship between the arm motion feature amount and the arm motion evaluation value at the determination time. The arm motion evaluation value model 525 is generated by the arm motion evaluation value calculation unit 535 or is updated each time the teacher data is acquired, for example.

The determination model 526 is a learning model used for determining whether it is a meal or non-meal from the heart rate evaluation value and the arm motion evaluation value. The determination model 526 is generated by using the absolute value of the difference between the heart rate evaluation value and the arm motion evaluation value, the arm motion evaluation value and the heart rate evaluation value, and information indicating whether it is the meal or non-meal at each determination time as teacher data, for example. The determination model 526 is generated by the determination unit 536 or is updated each time teacher data is acquired, for example.

FIG. 10 is a diagram illustrating an example of teacher data in Example 2. As illustrated in FIG. 10, in the teacher data in Example 2, the presence or absence of "meal", "heart rate evaluation value", and "arm motion evaluation value" at "determination time" are stored in association with each "determination time". The teacher data may include a heart rate evaluation value vector and an arm motion evaluation value vector described later, in addition to or instead of the heart rate evaluation value and the arm motion evaluation value. The teacher data may further include a difference between the absolute value of the heart rate evaluation value vector and the absolute value of the arm motion evaluation value vector.

The control unit 530 is a processing unit that controls overall processing of the detection device 500. The control unit 530 is realized, for example, in such a way that the program stored in an internal storage device is executed by the CPU, the MPU, or the like by using the RAM as a work area. For example, the control unit 530 may be realized by an integrated circuit such as the ASIC, the FPGA, or the like.

The control unit 530 includes the input and output unit 131, the heart rate feature amount calculation unit 132, the arm motion feature amount calculation unit 133, a heart rate evaluation value calculation unit 534, an arm motion evaluation value calculation unit 535, and a determination unit 536. The heart rate evaluation value calculation unit 534, the arm motion evaluation value calculation unit 535, and the determination unit 536 are also examples of an electronic circuit included in the processor and examples of a process to be executed by the processor.

The heart rate evaluation value calculation unit 534 refers to the heart rate evaluation value model 524 and calculates a heart rate evaluation value. The heart rate evaluation value calculation unit 534 collects the calculated heart rate evaluation values for each piece of time-series data and generates the heart rate evaluation value vector. The heart rate evaluation value vector is an example of a first evaluation value vector.

The arm motion evaluation value calculation unit 535 refers to the arm motion evaluation value model 525 and calculates the arm motion evaluation value. The arm motion evaluation value calculation unit 535 collects the calculated arm motion evaluation values for each piece of time-series data and generates an arm motion evaluation value vector. The arm motion evaluation value vector is an example of a second evaluation value vector.

The determination unit 536 refers to the determination model 526 to determine whether the determination time corresponds to a meal or not, by using the heart rate evaluation value vector and the arm motion evaluation value vector. When new teacher data is acquired, the determination unit 536 performs a learning process to be described later to generate or update a learning model.

Flow of Process

Figure 11:
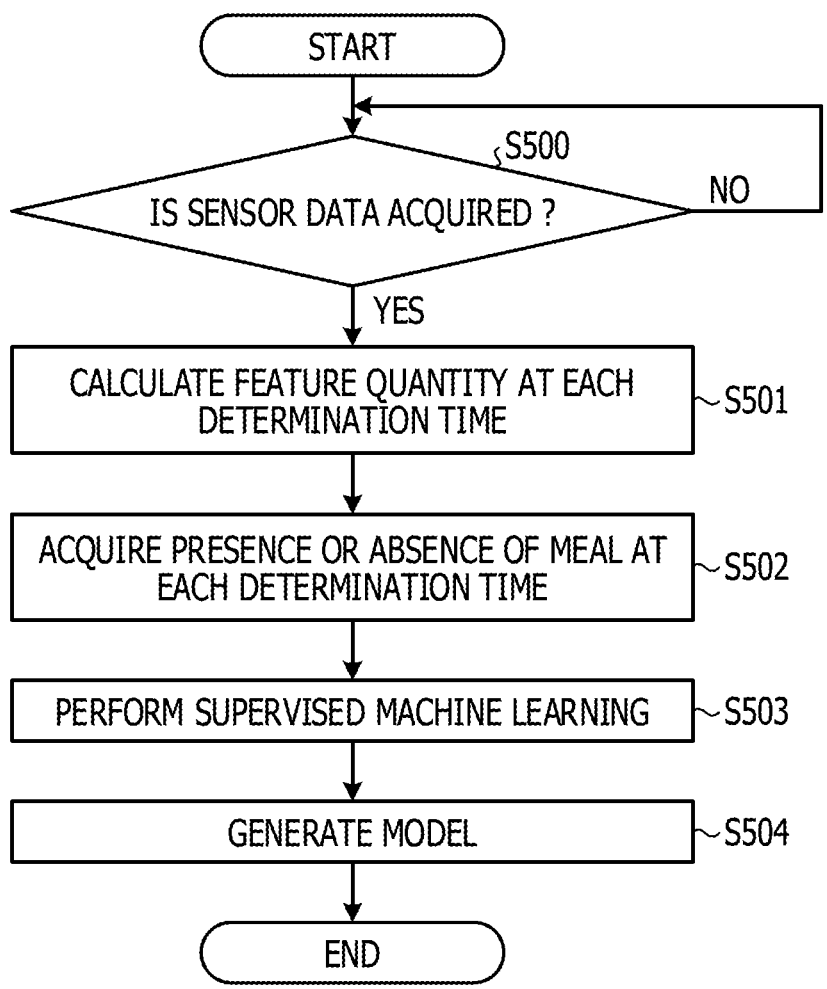
FIG. 11 is a flowchart illustrating an example of a learning process in Example 2.

Next, a process in Example 2 will be described with reference to FIG. 11. FIG. 11 is a flowchart illustrating an example of a learning process in Example 2. The learning process illustrated in FIG. 11 is executed every time new teacher data is acquired, for example.

First, as illustrated in FIG. 11, the input and output unit 131 of the detection device 500 waits until sensor data is acquired from the terminal device 200 through the communication I/F unit 110 (No in S500).

In a case where it is determined that the sensor data is acquired (Yes in S500), the input and output unit 131 outputs the acquired sensor data to the heart rate feature amount calculation unit 132 and the arm motion feature amount calculation unit 133. The heart rate feature amount calculation unit 132 calculates the heart rate feature amount at each determination time, using the acquired sensor data. Similarly, the arm motion feature amount calculation unit 133 calculates the arm motion feature amount at each determination time, using the acquired sensor data (S501).

Next, the determination unit 536 acquires teacher data relating to the presence or absence of the meal at each determination time (S502). Then, the determination unit 536 performs supervised machine learning using the teacher data (S503), generates a learning model (S504), and ends the process.

Processing Result

Figure 12:
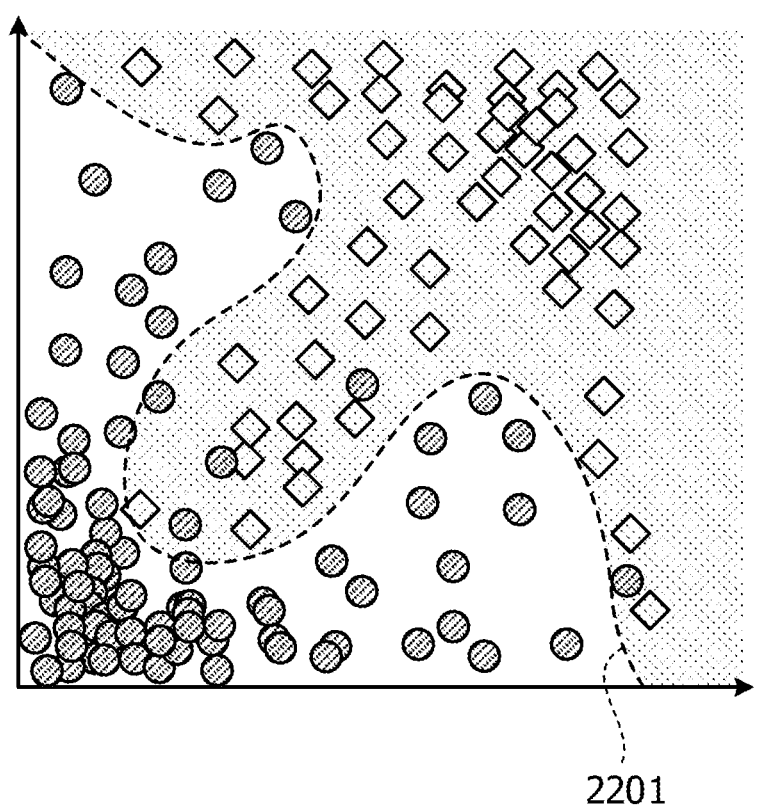
FIG. 12 is a diagram illustrating an example of a meal determination result in Example 2.

With reference to FIG. 12, description will be made on the meal determination result by the determination process using machine learning as described above. FIG. 12 is a diagram illustrating an example of a meal determination result in Example 2. As indicated by a reference numeral 2201 in FIG. 12, as a result of the determination using machine learning, erroneous detection and detection failure may be suppressed as compared with the case where a threshold value is used.

Effect

As described above, the detection device in Example 2 calculates the first evaluation value vector relating to the meal for each piece of time-series data of the heart rate. The detection device calculates the second evaluation value vector relating to the meal for each piece of time-series data of the movement of the arm. The detection device generates a meal estimation model for classifying arbitrary first evaluation value vector and second evaluation value vector into a meal or non-meal, by using classifications of the meal or non-meal corresponding to time-series data, the first evaluation value vector, and the second evaluation value vector as teacher data. The detection device classifies the first evaluation value vector and the second evaluation value vector into the meal or non-meal using the meal estimation model to thereby determine whether the target person has eaten a meal or not. With this, it is possible to accurately detect the meal compared with the configuration in which a threshold value is used.

Example 3

Although the embodiments of the present disclosure have been described so far, the present disclosure may be embodied in various different form in addition to the embodiments described above. Each of the illustrated processes is not limited to the order described above, but may be performed simultaneously in a range that does not contradict the process contents, and the processes may be performed while changing the order.

Figure 13:
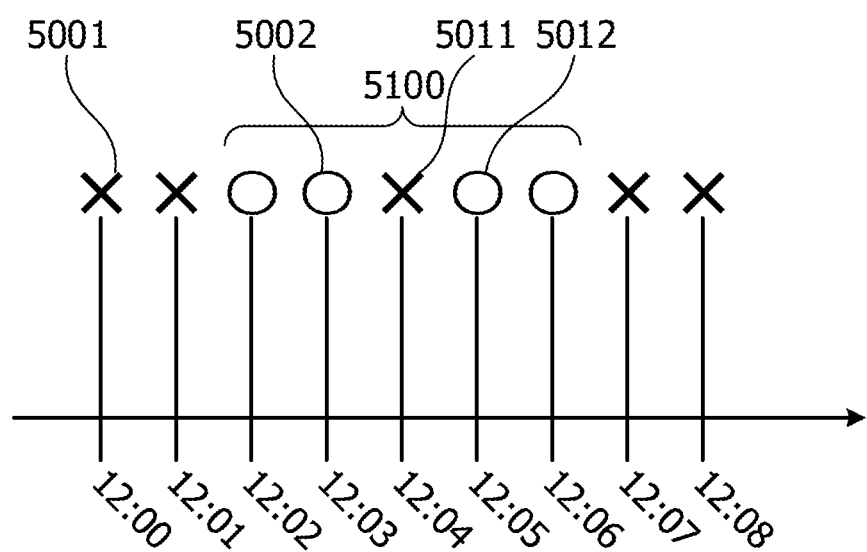
FIG. 13 is a diagram illustrating an example of a comparison of detection results with time zones before and after the determination time in Example 3.

In a case where the determination result of the presence or absence of meal at the specific determination time is different from the determination result at the time before and after the determination time, there is a high possibility that the determination result of the presence or absence of meal at the specific determination time is due to erroneous detection or detection failure. FIG. 13 is a diagram illustrating an example of a comparison of detection results with time zones before and after the determination time in Example 3. In FIG. 13, the symbol "X" at the determination time S001 indicates that it is determined to be non-meal intake at the determination time S001. Similarly, the symbol "O" at the determination time S002 indicates that the determination time S002 is determined to be meal.

In this case, a period S100 is considered to be a period during which the target person is eating a meal. However, at the determination time S011 included in the period S100, it is determined that the determination time S011 is the non-meal. In this case, in the detection device of Example 3, the determination time S011 may be determined to be "it is a meal" regardless of the detection result. As such, the meal determination result according to the detection result at the determination time before and after is updated to thereby make it possible to suppress deterioration of the determination system due to erroneous detection or detection failure.

In Example 2, the configuration for determining whether the target person is eating a meal at the determination time or not, by machine learning, is described, but is not limited thereto. A configuration for further determining the content or type of the meal of the target person may be adopted. Such a configuration may be realized by preparing teacher data which further includes items for classification or contents of meal, in addition to items as illustrated in FIG. 10.

FIG. 14 is a diagram illustrating an example of teacher data in Example 3. As illustrated in FIG. 14, the items "classification" and "content" of the meal are further stored in association with each other in teacher data, in addition to the presence or absence of "meal", the "heart rate evaluation value", and the "arm motion evaluation value" at the "determination time".

In FIG. 14, the "classification" categorizes meals such as "confectionery" and "staple food". The "content" indicates the content of the food that the target person ate. In Example 3, the determination unit 136 generates a learning model using teacher data as illustrated in FIG. 14. With this, it is possible to detect the classification and content of the meal, in addition to the presence or absence of meal. The teacher data may be configured in such a way that in addition to the classification and content of the meal, the amount of calories of the meal is given and caloric intake is detected using the arm motion evaluation value and the heart rate evaluation value, may be adopted.

The arm motion measurement device 10 and the heart rate measurement device 20 are not limited to the examples described above. For example, the arm motion measurement device 10 may use a gyro sensor instead of the acceleration sensor, as the motion sensor 11. In this case, the arm motion measurement device 10 acquires the motion of the arm of the target person using inertia data sensed by the gyro sensor.

As a heart rate sensor, a sensor other than a wearable type sensor may be adopted. For example, detection of the number of heartbeats may be realized in a non-contact state with the body part of the user by detecting the number of heartbeats from time-series change in luminance relating to an image in which a part of the user's body is imaged at a predetermined sampling frequency or detecting the Doppler frequency accompanying the heart rate using a radio frequency (RF) motion sensor.

Although the heart rate feature amount may not be calculated from the heartbeat, it is sufficient as long as the heart rate feature amount relates to a state of the heartbeat. For example, the RR interval may be calculated from a waveform of a pulse, its change, and electrocardiogram and may be matched with a value obtained by indexing the degree of fluctuation. The heart rate feature amount may be blood pressure or its change.

System

Each of configuration elements of the parts illustrated in the drawings is not necessarily physically configured as illustrated in the drawing. That is, a specific form of distribution and integration of the configuration elements is not limited to that illustrated in the drawing, and all or some of the parts may be distributed or integrated functionally or physically in an arbitrary unit according to various loads, usage conditions, and the like.

Furthermore, all or some of the various processing functions performed by each device may be executed on a CPU (or micro-computer such as the MPU, a micro controller unit (MCU) or the like). It goes without saying that all or some of the various processing functions may also be executed on a program analyzed and executed by the CPU (or microcomputer such as the MPU, the MCU or the like) or on hardware with wired-logic.

Standalone

In Example 1 described above, the case where it is constructed as a client server system including the arm motion measurement device 10, the heart rate measurement device 20, and the detection device 100 is exemplified, but is not limited thereto. For example, a series of processes from acquisition of heart rate data to estimation of the meal time may be executed on the arm motion measurement device 10, the heart rate measurement device 20, the detection device 100, or another computer in a stand-alone manner.

Application Example of System

In Example 1, the detection device 100 is included in the detection system 1, but the detection device 100 may not be included. That is, in a case where the terminal device 200 is installed as a wearable gadget or the like, the smartphone or the tablet terminal connected by short-distance wireless communication or the like with the wearable gadget may execute various kinds of processes other than acquisition of heart rate data, for example, estimation of the meal time.

Distribution and Integration

Each of configuration elements of the devices illustrated in the drawings may not be physically configured as illustrated in the drawings. That is, specific forms of distribution and integration of the configuration elements are not limited to that illustrated in the drawing, and all or some of the configuration elements may be distributed functionally or physically in arbitrary units according to various loads, usage conditions, and the like. For example, the input and output unit 131, the heart rate feature amount calculation unit 132, the arm motion feature amount calculation unit 133, the heart rate evaluation value calculation unit 134, the arm motion evaluation value calculation unit 135, and the determination unit 136 may be connected as an external device of the detection device 100 via a network.

Meal Detection Program

The various processes described in the embodiments described above may be realized by executing a program prepared in advance by a computer such as a personal computer or a workstation. Therefore, in the following, an example of a computer that executes a meal detection program having the same functions as those in the embodiments described above will be described with reference to FIG. 15.

Figure 15:
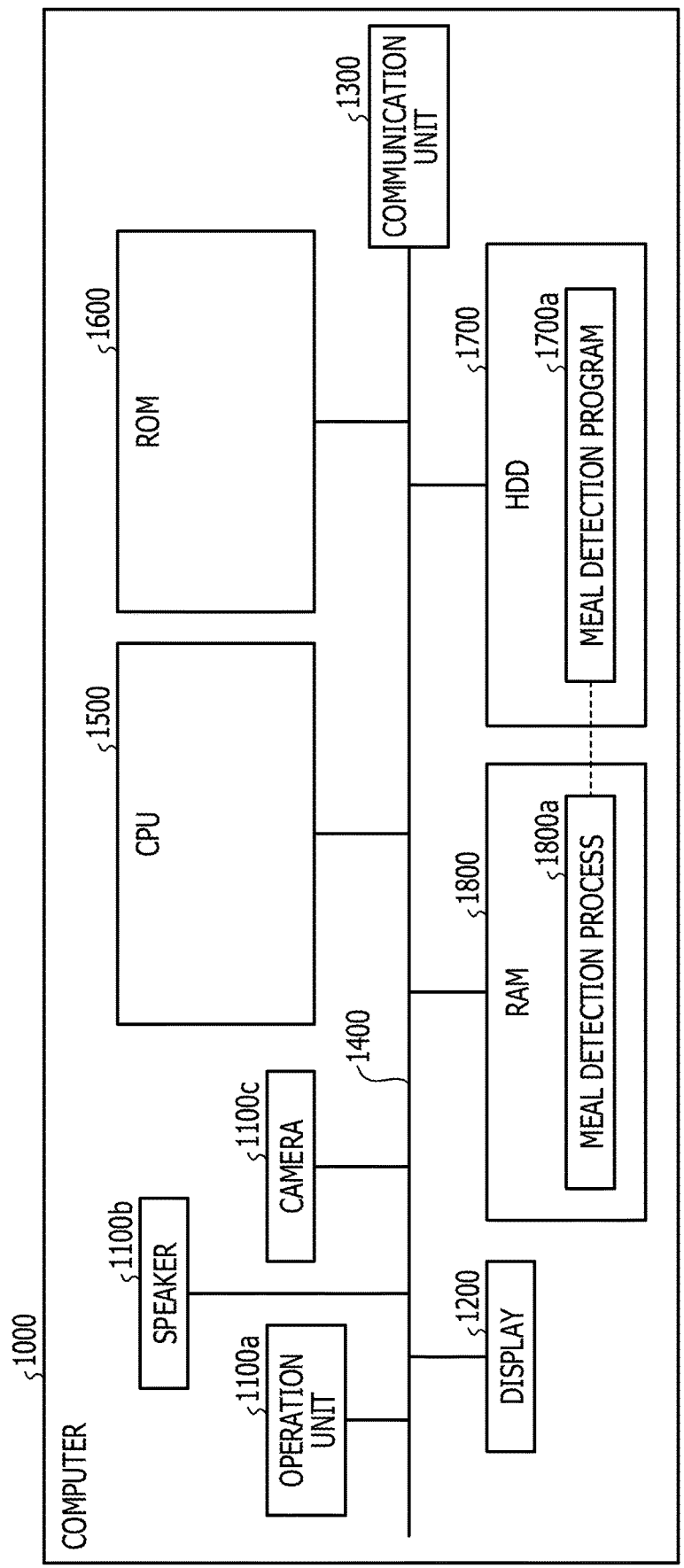
FIG. 15 is a diagram illustrating an example of a hardware configuration of a computer that executes a meal detection program.

FIG. 15 is a diagram illustrating a hardware configuration example of a computer that executes the meal detection program. As illustrated in FIG. 15, a computer 1000 includes an operation unit 1100*a*, a speaker 1100*b*, a camera 1100*c*, a display 1200, and a communication unit 1300. Furthermore, the computer 1000 includes a CPU 1500, a ROM 1600, an HDD 1700, and a RAM 1800. The respective units 1100 to 1800 are connected via a bus 1400.

In the HDD 1700, as illustrated in FIG. 15, a meal detection program 1700*a* that exhibits the same functions as the input and output unit 131, the heart rate feature amount calculation unit 132, the arm motion feature amount calculation unit 133, the heart rate evaluation value calculation unit 134, the arm motion evaluation value calculation unit 135, and the determination unit 136 illustrated in Example 1 is stored. The meal detection program 1700*a* may be integrated or separated similarly as with the respective components of the input and output unit 131, the heart rate feature amount calculation unit 132, the arm motion feature amount calculation unit 133, the heart rate evaluation value calculation unit 134, the arm motion evaluation value calculation unit 135, and the determination unit 136 illustrated in FIG. 7. That is, some pieces of data illustrated in Example 1 may not be stored in the HDD 1700, and data to be used for a process may be stored in the HDD 1700.

Under such a circumstance, the CPU 1500 reads the meal detection program 1700*a* from the HDD 1700 and develops the meal detection program 1700*a* in the RAM 1800. As a result, the meal detection program 1700*a* functions as a meal detection process 1800*a* as illustrated in FIG. 15. The meal detection process 1800*a* develops various pieces of data read from the HDD 1700 into an area allocated to the meal detection process 1800*a* in the storage area of the RAM 1800 and executes various processes using the developed various pieces of data. For example, as an example of the process executed by the meal detection process 1800*a*, the process illustrated in FIG. 8 and the like are included. In the CPU 1500, some of the processing units described in Example 1 may not be operated, and it suffices that the processing unit corresponding to a process to be executed is virtually realized.

The meal detection program 1700*a* described above may not be stored in the HDD 1700 or the ROM 1600 from the beginning. For example, each program is stored in a "portable physical medium" such as a flexible disk, so-called an FD, CD-ROM, DVD disk, magneto-optical disk, IC card or the like, to be inserted in the computer 1000. Then, the computer 1000 may obtain and execute each program from these portable physical media. Each program may be stored in another computer or server device connected to the computer 1000 via a public line, the Internet, a LAN, a WAN, and the like, and the computer 1000 may acquire each program from the other computer or server device and execute the program.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A meal detection method executed by a processor of a computer, the meal detection method comprising:

acquiring first sensing data from a first sensor configured to detect a motion of an arm of a target person;

acquiring second sensing data from a second sensor configured to detect a heart rate of the target person;

calculating a first evaluation value that is a first degree of similarity between a first feature amount calculated from the first sensing data and a pattern of movement of the arm that occurs when eating a meal as likelihood that the meal is performed;

calculating a second evaluation value that is a second degree of similarity between a second feature amount calculated from the second sensing data and a pattern of the heart rate that occurs when eating the meal as likelihood that the meal is performed; and determining whether the target person has eaten the meal or not by confirming whether the first evaluation value and the second evaluation value satisfy a predetermined condition.

2. The meal detection method according to claim 1,
wherein the determining includes determining that, when a difference between the first evaluation value and the second evaluation value is equal to or less than a predetermined first threshold value, the target person has eaten the meal.

3. The meal detection method according to claim 1,
wherein the determining includes determining that, when the difference between the first evaluation value and the second evaluation value is equal to or less than the predetermined first threshold value and the first evaluation value and the second evaluation value are equal to or greater than a predetermined second threshold value, the target person has eaten the meal.

4. The meal detection method according to claim 1,
wherein the determining includes determining that, when one of the first evaluation value and the second evaluation value is equal to or greater than a predetermined third threshold value, the target person has eaten the meal.

5. The meal detection method according to claim 1,
wherein the determining includes determining whether the target person has eaten the meal or not, by classifying the first evaluation value and the second evaluation value into the meal or a non-meal by using a meal estimation model for classifying the first evaluation value and the second evaluation value into the meal or the non-meal.

6. The meal detection method according to claim 5,
wherein the calculating of the first evaluation value includes calculating a first evaluation value vector relating to the meal from time-series data of the heartbeat,
the calculating of the second evaluation value includes calculating a second evaluation value vector relating to the meal from time-series data of the motion of the arm, and
the meal detection method further comprises
generating the meal estimation model by using classifications of the meal or the non-meal corresponding to the time-series-data, the first evaluation value vector, and the second evaluation value vector as teacher data.

7. The meal detection method according to claim 6,
wherein the generating of the meal estimation model includes generating the meal estimation model by further using a difference between absolute values of the first evaluation value vector and the second evaluation value vector.

8. The meal detection method according to claim 1,
wherein the determining includes:
classifying a time zone to be determined into the meal when an immediately preceding time zone and an immediately following time zone of the time zone to be determined are classified into the meal, and
classifying the time zone to be determined into the non-meal when the immediately preceding time zone and the immediately following time zone are classified into the non-meal.

9. The meal detection method according to claim 1,
wherein the determining includes specifying a content or type of the meal using a learning model for classifying any of the first evaluation value and the second evaluation value with respect to the content or type of the meal.

10. A non-transitory computer-readable storage medium having stored therein a program for meal detection, the program executes a process comprising:
acquiring first sensing data from a first sensor configured to detect a motion of an arm of a target person;
acquiring second sensing data from a second sensor configured to detect a heart rate of the target person;
calculating a first evaluation value that is a first degree of similarity between a first feature amount calculated from the first sensing data and a pattern of movement of the arm that occurs when eating a meal as likelihood that the meal is performed;
calculating a second evaluation value that is a second degree of similarity between a second feature amount calculated from the second sensing data and a pattern of the heart rate that occurs when eating the meal as likelihood that the meal is performed; and
determining whether the target person has eaten the meal or not by confirming whether the first evaluation value and the second evaluation value satisfy a predetermined condition.

11. The storage medium according to claim 10,
wherein the determining includes determining that, when a difference between the first evaluation value and the second evaluation value is equal to or less than a predetermined first threshold value, the target person has eaten the meal.

12. The storage medium according to claim 10,
wherein the determining includes determining that, when the difference between the first evaluation value and the second evaluation value is equal to or less than the predetermined first threshold value and the first evaluation value and the second evaluation value are equal to or greater than a predetermined second threshold value, the target person has eaten the meal.

13. The storage medium according to claim 10,
wherein the determining includes determining that, when one of the first evaluation value and the second evaluation value is equal to or greater than a predetermined third threshold value, the target person has eaten the meal.

14. The storage medium according to claim 10,
wherein the determining includes determining whether the target person has eaten the meal or not, by classifying the first evaluation value and the second evaluation value into the meal or a non-meal by using a meal estimation model for classifying the first evaluation value and the second evaluation value into the meal or the non-meal.

15. The storage medium according to claim 14,
wherein the calculating of the first evaluation value includes calculating a first evaluation value vector relating to the meal from time-series data of the heartbeat,
the calculating of the second evaluation value includes calculating a second evaluation value vector relating to the meal from time-series data of the motion of the arm, and
the meal detection method further comprises
generating the meal estimation model by using classifications of the meal or the non-meal corresponding to the time-series-data, the first evaluation value vector, and the second evaluation value vector as teacher data.

16. The storage medium according to claim 15,
wherein the generating of the meal estimation model includes generating the meal estimation model by further using a difference between absolute values of the first evaluation value vector and the second evaluation value vector.

17. The storage medium according to claim 10, wherein the determining includes:
classifying a time zone to be determined into the meal when an immediately preceding time zone and an immediately following time zone of the time zone to be determined are classified into the meal, and
classifying the time zone to be determined into the non-meal when the immediately preceding time zone and the immediately following time zone are classified into the non-meal.

18. The storage medium according to claim 10, wherein the determining includes specifying a content or type of the meal using a learning model for classifying any of the first evaluation value and the second evaluation value with respect to the content or type of the meal.

19. A meal detection system, comprising:
a first sensor configured to detect a motion of an arm of a target person,
a second sensor configured to detect a heart rate of the target person, and
a processor coupled to the first sensor and the second sensor, and configured to:
acquire first sensing data from the first sensor,
acquire second sensing data from the second sensor,
calculate a first evaluation value that is a first degree of similarity between a first feature amount calculated from the first sensing data and a pattern of movement of the arm that occurs when eating a meal as likelihood that the meal is performed;
calculate a second evaluation value that is a second degree of similarity between a second feature amount calculated from the second sensing data and a pattern of the heart rate that occurs when eating the meal as likelihood that the meal is performed; and
determine whether the target person has eaten the meal or not by confirming whether the first evaluation value and the second evaluation value satisfy a predetermined condition.

* * * * *